United States Patent [19]

London et al.

[11] Patent Number: 5,516,911
[45] Date of Patent: May 14, 1996

[54] FLUORESCENT INTRACELLULAR CALCIUM INDICATORS

[75] Inventors: Robert E. London; Louis A. Levy, both of Chapel Hill; Elizabeth Murphy, Durham, all of N.C.

[73] Assignee: The United States of America as represented by the Department of Health and Human Services, Washington, D.C.

[21] Appl. No.: 175,590

[22] Filed: Dec. 30, 1993

[51] Int. Cl.$^6$ .................. C07D 263/34; C07C 205/06; C07C 229/40
[52] U.S. Cl. .................. 548/236; 548/452; 549/223; 560/21; 562/433; 562/452; 562/887
[58] Field of Search .................. 562/452, 887, 562/433; 560/21; 549/223; 548/452, 236

[56] References Cited

U.S. PATENT DOCUMENTS

| | | | |
|---|---|---|---|
| 4,397,944 | 8/1983 | Komura et al. | 435/4 |
| 4,603,209 | 7/1986 | Tsien et al. | 548/236 |
| 4,788,137 | 11/1988 | Reinherz et al. | 435/7 |
| 4,849,362 | 7/1989 | DeMarinis et al. | 436/63 |
| 4,916,060 | 4/1990 | Weaver | 435/29 |
| 4,945,171 | 7/1990 | Haughland et al. | 549/224 |

FOREIGN PATENT DOCUMENTS

| | | |
|---|---|---|
| 0177202 | 9/1985 | European Pat. Off. . |
| 0314480 | 10/1988 | European Pat. Off. . |

OTHER PUBLICATIONS

Smith et al PNAS (1983) 80(23) 7178–7182.
Molecular Probes Inc. Set 20: Calcium Indicators, Chelators and Ionophores 113–141 (1992–1994).
Smith et al J. Chem. Soc. (1993) p. 1187.
Clarke, S. D., et al., "Design and Properties of New $^{19}$F NMR Ca$^{2+}$ Indicators: Modulation of the Affinities of BAPTA Derivatives via Alkylation", *J. Chem. Soc.:1187–1194*.
Smith, G. A., et al., "The Design and Properties of a Series of Calcium Indicators which Shift from Rhodamine–like to Fluorescein–like Fluorescence on Binding Calcium", *J. Chem. Soc., :1195–1204 (1993)*.

Smith, G. A., et al., "A New $^{19}$F NMR Indicator for Intracellular Sodium", *J. Chem. Soc.,:1205–1209 (1993)*.
P. H. Cobbold and T. J. Rink, "Fluorescence and bioluminescence measurement of cytoplasmic free calcium", 248:313–328 (1987).
Minta, A., et al., "Fluorescent Indicators for Cytosolic Calcium Based on Rhodamine and Fluorescein Chromophores", *J. of Biol. Chem., 264(14):8171–8178 (1989)*.
Grynkiewicz, G., et al., "A New Generation of Ca$^{2+}$ Indicators with Greatly Improved Fluorescence Properties", *J. of Biol. chem., 260(6):3440–3450 (1985)*.
Roger Y. Tsien, "New Calcium Indicators and Buffers with High Selectivity against Magnesium and Protons: Design, Synthesis, and Properties of Prototype Structures", *Biochemistry 19:2396–2404 (1980)*.
Smith, G. A., et al. "Intracellular calcium measurements by $^{19}$F NMR of fluorine–labeled chelators", *Proc. Natl. Acad. Sci. USA, 80:7178–7182 (1983)*.
Roger. Y. Tsien, "Fluorescent Probes of Cell Signaling", *Am. Rev. Neurosci., 12:227–253 (1989)*.
W. G. Wier, "Cytoplasmic [Ca$^{2+}$] in Mammalian Ventricle: Dynamic Control by Cellular Processes", *Annu. Rev. Physiol. 52:467–485 (1990)*.
Paul A. Negulescu and Terry E. Machen, "Intracellular Ion Activities and Membrane Transport in Parietal Cells Measured with Fluorescent Dyes", *Meth. in Enzymology, 192:38–81 (1990)*.
Article from *Molecular Probes, Inc.*, Set 20: Calcium Indicators, Chelators and Ionophores, "Calcium Indicators, Chelators and Ionophores", 113–141 (1992–1994).

*Primary Examiner*—Paul F. Shaver
*Assistant Examiner*—Joseph M. Conrad, III
*Attorney, Agent, or Firm*—Townsend and Townsend and Crew

[57] ABSTRACT

A new class of calcium-specific, NMR-active and/or fluorescent indicators having a high dissociation constant is described. Methods of determining intracellular calcium ion concentration using $^{19}$F NMR spectroscopy or optical methods are also provided.

5 Claims, 3 Drawing Sheets

FLUORESCENT INTRACELLULAR CALCIUM INDICATORS

BACKGROUND OF THE INVENTION

1. Field of the Invention

This invention relates to compositions and methods useful for measuring intracellular calcium, and, more specifically to novel fluorinated aromatic compounds.

2. Background

Calcium is a key element in the regulation of numerous cellular processes. Calcium is known to control the contraction of muscle, the secretion of hormones from gland cells and transmitters from nerve synapses, plus a multitude of other functions. For example, the development of tension in vascular smooth muscle and cardiac muscle is dependent on a rise in free cytosolic calcium ion ($Ca^{++}$) levels.

Variations of the calcium ion concentration in the cytosol of cells exert profound effects on cellular metabolism, both in normal cell physiology, as well as in the mediation of the toxicito of various chemical and physical agents. For example, it is known that changes in levels of intracellular calcium ion are linked to physiological events as diverse as platelet aggregation, exocytosis and cell proliferation.

The role of calcium ion in important cellular processes has directed investigation into the development of techniques for measuring calcium ion levels in living cells. The use of optical indicators, in particular polycarboxylate chelating compounds, are among the most reliable methods of calcium ion detection currently available. These polycarboxylate compounds are introduced to the cell as ester derivatives which penetrate the cell membrane. Inside the cell, the esters are cleaved enzymatically to give polycarboxylate ions which are impermeable (or permeable only at a slow rate) to the cell membrane. Thus, once inside the cell, the polycarboxylate ions cannot escape at any appreciable rate. When the polycarboxylate compounds bind to calcium ion, a change in their spectral properties is produced. The magnitude of this spectral shift may be correlated to the local calcium ion concentration and thus be used to measure the amount of bound calcium ion. From a knowledge of this correlation, the intracellular calcium concentration can be determined.

Currently one popular embodiment of these methods includes monitoring the spectral properties of BAPTA (1,2-bis( 2-aminophenoxy)ethane- N,N,N',N'-tetraacetic acid) or analogs thereof, such as fura-2, indo-1, and fluo-2. These compounds can be easily loaded into cells by hydrolysis of their membrane-permeable esters (here, R is lower alkyl or acetoxymethyl).

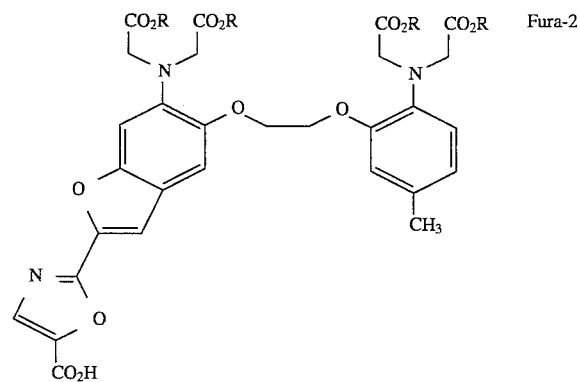

Fura-2

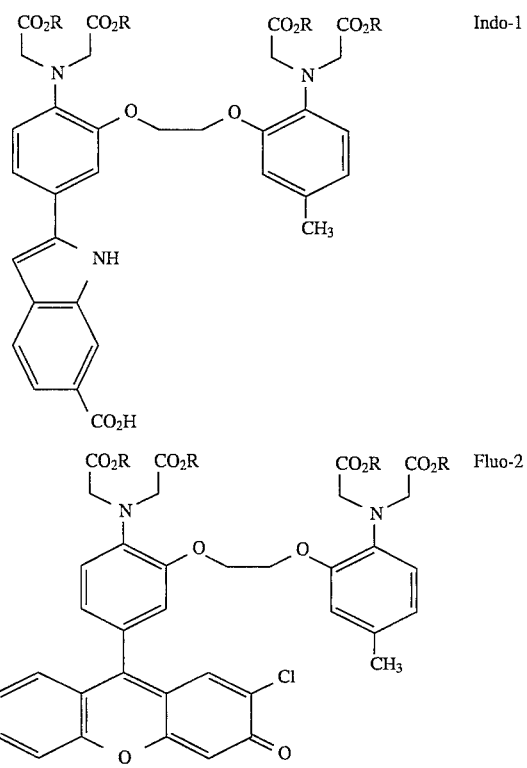

Indo-1

Fluo-2

Such conventional calcium ion indicators are designed to determine cytosolic calcium ion levels only. Unfortunately, the basal calcium ion levels in the cytosol and in various organelles within the cell can differ dramatically; hence, conventional indicators may not be suitable for carrying out measurements in organelles. For example, the calcium ion concentrations in the sarcoplasmic reticulum (SR) and endoplasmic reticulum (ER) are thought to be several orders of magnitude greater than in the cytosol. Ionized calcium concentrations in the SR and the ER are of great interest. Calcium release from the SR is responsible for contraction in muscle, and the regulation of SR calcium uptake and release are of importance in muscle function. In addition, ER or related calcium sequestering organelles are important in receptor mediated calcium signalling in non-muscle cells. Yet present intracellular calcium ion indicators such as fura-2 are saturated at the calcium levels normally present in the SR and ER. Also, the use of high dissociation constant ($K_D$) calcium indicators for cytosolic calcium ion measurements has several important advantages: (1) reduced buffering of intracellular calcium and reduced perturbation of calcium transients, and (2) measurement of more rapid calcium transients than with ordinary calcium chelators. Hence, a need for higher dissociation constant calcium ion indicators exists.

In addition, the role of calcium ions in maintaining normal physiological function and in the mediation of pathological conditions is barely understood. Nevertheless, it is already clear that there are significant perturbations in cytosolic calcium levels and transients which are associated with disease states. For example, studies in perfused rat heart have demonstrated that a significant increase in the level of cytosolic free calcium occurs prior to irreversible cell injury (Steenbergen et al., *Circ. Res.* 60, 700; 1987). Indeed, there is much literature suggesting that an elevation of cytosolic calcium ion concentration plays a general role in producing irreversible cell injury. Hence, it would be extremely useful if techniques and reagents were available which could be extended to the study of such pathological states. Such reagents would have to provide reliable measurements under conditions of high intracellular $Ca^{+2}$ concentrations (i.e., have a high $K_D$) and ideally have the ability to be introduced selectively into specific organelles. If appropriate and non-injurious loading conditions could be developed, these could also be used for the determination of free calcium ion concentrations in human subjects. This would be a major breakthrough for understanding the role of calcium ion in normal and pathological states, and potentially for the diagnosis of a bread range of diseases.

To date, conventional methods and agents have not proven to be effective for determining either the high levels of calcium ions associated with some pathological conditions or the calcium ion level in organelles of interest. For these reasons it would be desirable to provide improved calcium ion indicators and methods, which avoid the disadvantages of these conventional agents and methods, while providing effective means for determining calcium ion concentration.

SUMMARY OF THE INVENTION

The present invention includes a new class of calcium specific chromophoric or fluorescent indicator dyes having excitation and emission wavelengths in the ultraviolet or visible portions of the electromagnetic spectrum. The novel chromophoric or fluorescent indicator dyes of the invention contain at least one aromatic ring having a fluorine atom located ortho to a phenolic oxygen. Other positions of the aromatic rings may carry chromophoric or fluorescent substituents whose spectral properties are sensitive to complexation of calcium ion by the polycarboxylate chelating moiety. Quantitation of the intracellular calcium ion concentration is achieved by monitoring changes in these spectral properties.

In another embodiment, the present invention includes a method of determining intracellular calcium ion concentration which comprises correlating the $^{19}F$ NMR signals of fluoro-substituted compounds carrying a second fluorine at a position meta or para to the phenolic oxygen with calcium ion concentration. These compounds make intracellular calcium measurements available for a much wider variety of instrumentation and applications than heretofore available with currently available calcium ion probes. The compounds of the invention are particularly useful for the determination of calcium ion concentration using $^{19}F$ NMR spectroscopy, flow cytometry, and quantitative fluorescence techniques.

In one embodiment, the invention includes compounds useful for the determination of intracellular $Ca^{+2}$ concentration using $^{19}F$ NMR. Such compounds are shown in Formula I:

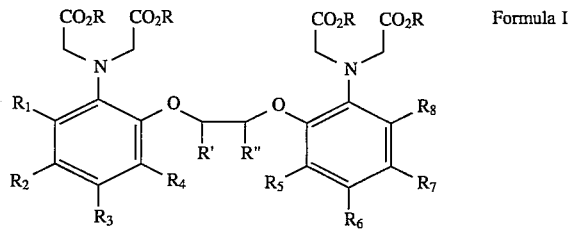

wherein R is selected from the group consisting of hydrogen, acetoxymethyl, and a sodium, potassium or lithium cation;

R' and R" are independently selected from the group consisting of hydrogen and lower alkyl or R' and R", and the carbon atoms to which they are bonded, may be constituents of a 5-membered or 6-membered carbocyclic or heterocyclic ring; and $R_1$–$R_8$ are independently selected from the group consisting of hydrogen, lower alkyl, aryl, substituted alkyl, substituted aryl, alkoxy, amino, carboxyl, cyano, halogen, hydroxyl, nitro and chromophoric or fluorescent substituents capable of functioning as optical indicators;

provided at least one of $R_4$ and $R_5$ is fluorine.

In a preferred embodiment, both $R_4$ and $R_5$ are fluorine. A second preferred embodiment of the invention, which is a useful high $K_D$ calcium chelator for NMR studies, includes compounds wherein R' and R" are selected independently from the group consisting of hydrogen and lower alkyl, and $R_3$–$R_6$ are fluorine, such as that shown in Formula II, 1,2-bis(2-amino-5,6-difluorophenoxy)ethane-N,N,N',N'-tetraacetic acid (TFBAPTA):

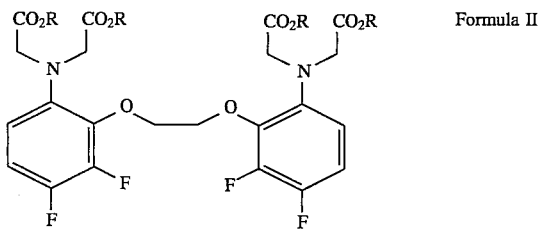

In still another embodiment, the present invention includes compounds in which at least one of $R_1$–$R_8$ is selected from the group consisting of chromophoric or fluorescent substituents capable of functioning as optical indicators and at least one of $R_4$ or $R_5$ is fluorine. These compounds are useful chromophoric or fluorescent calcium ion indicators.

A preferred embodiment of these compounds is obtained when $R_3$ is selected from the group consisting of chromophoric or fluorescent substituents that are capable of functioning as optical indicators, and $R_5$ is fluorine.

Especially preferred are those embodiments wherein $R_3$ is 6-carboxyindol-2-yl or 2,7-dichloro-6-hydroxy-3H-xanthen-3-one-9-yl.

In yet another embodiment, useful fluorescent calcium ion indicators of this invention will comprise compounds wherein $R_3$ is 6-carboxyindol-2-yl, shown in Formula III.

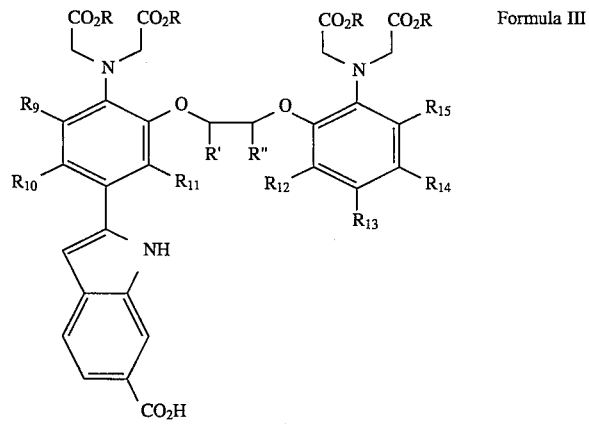

wherein:

R is selected from the group consisting of hydrogen, acetoxymethyl, and a sodium, potassium or lithium cation;

R' and R" are independently selected from the group consisting of hydrogen and lower alkyl or R' and R", and the carbon atoms to which they are bonded, may be constituents of a 5-membered or 6-membered carbocyclic or heterocyclic ring; and $R_9$–$R_{15}$ are selected independently from the group consisting of hydrogen, lower alkyl, aryl, substituted alkyl, substituted aryl, alkoxy, amino, carboxyl, cyano, halogen, hydroxyl, and nitro;

provided at least one of $R_{11}$ or $R_{12}$ is fluorine.

In yet a further embodiment, the invention includes the calcium ion indicator shown in Formula IV, where $R_3$ is a derivative of 3H-xanthen-3-one-9-yl:

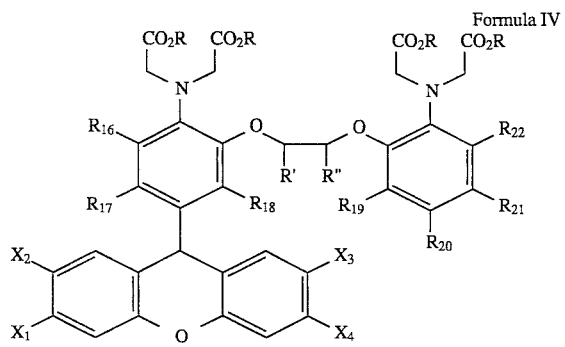

Formula IV wherein:

R is selected from the group consisting of hydrogen, acetoxymethyl, and a sodium, potassium or lithium cation;

R' and R" are independently selected from the group consisting of hydrogen and lower alkyl, or R' and R", and the carbon atoms to which they are bonded, may be constituents of a 5-membered or 6-membered carbocyclic or heterocyclic ring; and $R_{16}$–$R_{22}$ are selected independently from the group consisting of hydrogen, lower alkyl, aryl, substituted alkyl, substituted aryl, alkoxy, amino, carboxyl, cyano, halogen, hydroxyl, and nitro;

$X_1$ and $X_4$ are selected independently from the group consisting of amino, alkoxy, hydroxy, mercapto or alkylsiloxy; in addition, $X_1$ and $X_4$, together with the carbon atoms to which they are bound, may be selected independently from the group consisting of carbonyl, oxime, or imine; and $X_2$ and $X_3$ are selected independently from the group consisting of hydrogen, halogen or alkoxy; and provided at least one of $R_{18}$ or $R_{19}$ is fluorine.

In still yet another aspect, the invention includes calcium ion indicators comprising a compound of Formula V:

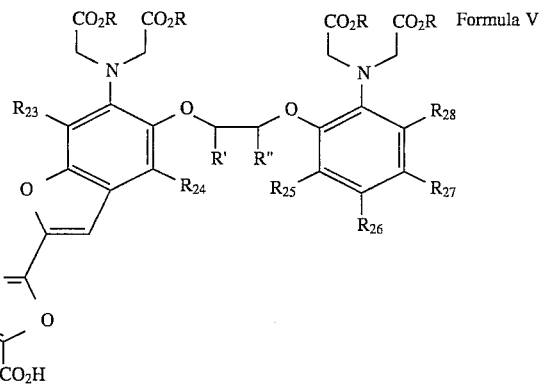

Formula V wherein:

R is selected from the group consisting of hydrogen, acetoxymethyl, and a sodium, potassium or lithium cation;

R' and R" are independently selected from the group consisting of hydrogen and lower alkyl, or R' and R", and the carbon atoms to which they are bonded, are constituents of a 5-membered or 6-membered carbocyclic or heterocyclic ring; and $R_{23}$–$R_{28}$ are selected independently from the group consisting of hydrogen, lower alkyl, aryl, substituted alkyl, substituted aryl, alkoxy, amino, carboxyl, cyano, halogen, hydroxyl, and nitro;

provided at least one of $R_{24}$ or $R_{25}$ is fluorine. A preferred embodiment of a compound of Formula V is obtained when $R_{25}$ is fluorine.

In yet another embodiment, the present invention includes a compound having the structure shown in Formula VI:

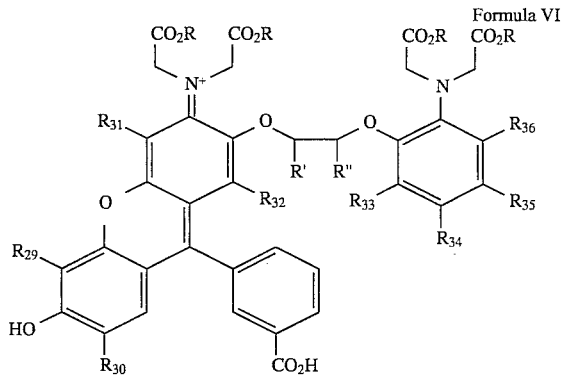

Formula VI wherein R is selected from the group consisting of hydrogen, acetoxymethyl, and a sodium, potassium or lithium cation; R' and R" are independently selected from the group consisting of hydrogen and lower alkyl; and R' and R", and the carbon atoms to which they are bonded, may be constituents of a 5-membered or 6-membered carbocyclic or heterocyclic ring. $R_{29}$–$R_{36}$ may be selected independently from the group consisting of hydrogen, lower alkyl, aryl, substituted alkyl, substituted aryl, alkoxy, amino, carboxyl, cyano, halogen, hydroxyl, and nitro. However, at least one of $R_{32}$ or $R_{33}$ must be fluorine.

The present invention also includes methods of determining intracellular calcium ion concentrations, wherein a compound of Formula I is introduced to a cell and the spectrum of the compound is recorded. The features of the recorded spectrum are compared with the spectral features of the compound at known calcium ion concentrations from which the intracellular ion concentration is calculated.

These and other aspects and details of the invention will become apparent when the detailed description of the invention is considered with the accompanying drawings.

DESCRIPTION OF THE PREFERRED EMBODIMENT

I. Definitions and General Parameters

Figure 1:
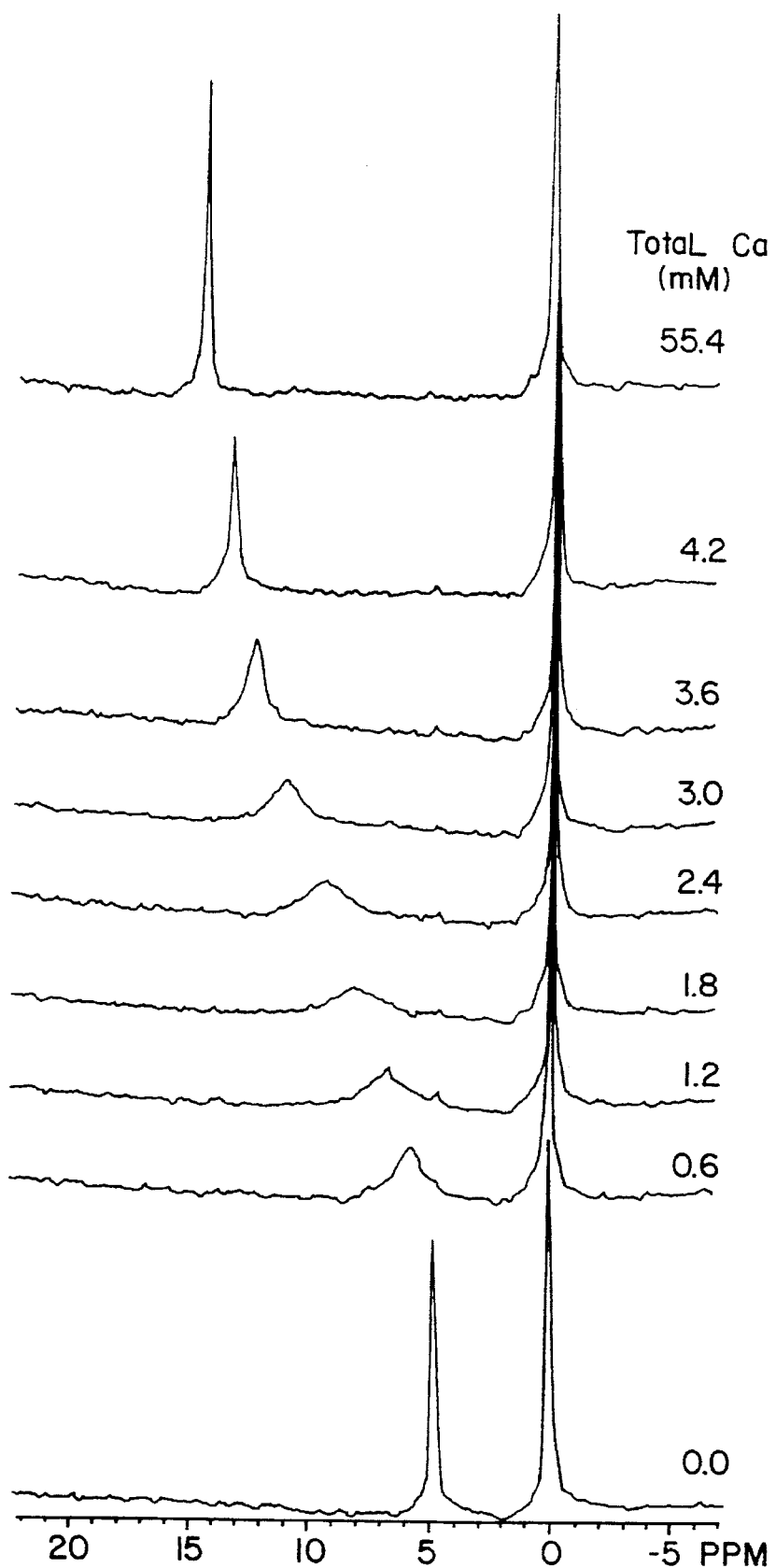
FIG. 1 shows a $^{19}$F NMR spectra of a solution containing 1.75 mM 5,5', 6,6'-tetrafluoro-BAPTA (TFBAPTA), 120 mM KCl, 20 mM NaCl, 10 mM Tris-Hepes (pH 7.2) as the total calcium concentration is varied from 0 to 55.4 mM. Total ionized calcium concentrations are listed on the left of the spectra.

The following definitions are set forth to illustrate and define the meaning and scope of the various terms used to describe the invention herein.

"Calcium ion" or "$Ca^{+2}$" refers to intracellular free calcium.

For use herein, "dye" and "indicator" are used interchangeably.

As used herein "BAPTA" means 1,2-bis(2-amino-phenoxy)ethane-N,N,N'N'-tetraacetic acid.

As used herein "BAPTA-like" means substituted derivatives of BAPTA which retain the essential characteristic of two bis(carboxymethyl)amino-substituted phenyl rings, said rings being linked at the positions ortho the amine through a four atom bridge.

The term "fluorescent substituent" refers to a chemical grouping which confers upon a compound the ability to emit light of a given wavelength after being irradiated with light, usually of a shorter wavelength than the emitted light. Preferred fluorescent substituents include those which undergo an emission or excitation shift or a change in spectral intensity (altered quantum efficiency) upon calcium ion complexation.

The term "chromophoric substituent" refers to a chemical grouping which confers upon a compound the ability to absorb light. Typical chromophoric and fluorescent substituents include groups such as the fluoresceins, rhodamines, rhodols, acridines, coumarins, pyrenes, benzofurans and indoles. Preferred substituents include 6-carboxyindol-2-yl; 2,7-dichloro-6-hydroxy-3H-xanthene-3-one-9-yl.

The term "optical indicator" refers to a chemical compound or moiety which produces a detectable signal in the visible or ultraviolet portion of the electromagnetic spectrum.

"Lower alkyl" refers to a cyclic, branched or straight chain alkyl group of one to six carbon atoms, which can optionally be unsubstituted or substituted with, e.g., amino, nitro, cyano, sulfonic acid, carbonyl, halogen, lower alkyl, lower alkoxy, lower alkylthio, trifluoromethyl, lower acyloxy, and hydroxyl. This term is further exemplified by such groups as methyl, ethyl, n-propyl, i-propyl, n-butyl, t-butyl, i-butyl (or 2-methylpropyl), cyclopropylmethyl, i-amyl, n-amyl, and hexyl.

"Alkoxy" refers to the group —$OR_1$ wherein $R_1$ is a lower alkyl group.

"Amino" refers to the group —$NR_1R_2$, where $R_1$ and $R_2$ are independently hydrogen, lower alkyl, or aryl.

"Aryl" or "Ar" refers to an aromatic carbocyclic group having a single ring (e.g., phenyl) or multiple condensed rings in which at least one ring is aromatic, (e.g., 1,2,3,4-tetrahydronaphthyl, naphthyl, or anthryl), which can optionally be unsubstituted or substituted with, e.g., amino, nitro, cyano, sulfonic acid, carbonyl, halogen, lower alkyl, lower alkoxy, lower alkylthio, trifluoromethyl, lower acyloxy, and hydroxyl.

"Carboxyl" or "carboxylic acid" refers to the group —COOH.

"Cyano" refers to the group —CN.

"Halogen" refers to fluorine, bromine, chlorine, and iodine atoms.

"Heterocycle" or "heterocyclic ring" refers to a saturated, unsaturated, or aromatic carbocyclic group having a single ring (e.g., morpholino, pyridyl or furyl) or multiple condensed rings (e.g., quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, lower alkylthio, trifluoromethyl, lower acyloxy, and hydroxyl. The term "heteroaryl" or "HetAr" refers to a heterocycle in which at least one heterocyclic ring is aromatic.

"Hydroxy or hydroxyl" refer to the group —OH.

"Mercapto", "sulphydryl", or "thiol" refers to the group —SH.

"Nitro" refers to the group —$NO_2$.

"Oxime" refers to the group =NOR, where R is hydrogen, alkyl, aryl, heteroaryl, arylalkyl or heteroarylalkyl.

"Imine" refers to the group =NR, where R is hydrogen, alkyl, aryl, heteroaryl, arylalkyl or heteroarylalkyl.

"Stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

Compounds of formula I–VI are generally named and numbered as illustrated below. For example, a compound of Formula II where R is hydrogen is named 1,2-bis(2-amino-5,6-difluorophenoxy) ethane-N,N,N',N'-tetraacetic acid.

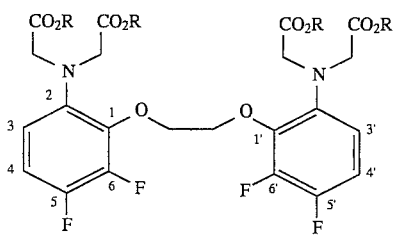

II. Calcium Specific Indicators

The present invention includes compounds and methods for determining the concentration of calcium ion in a sample using $^{19}F$ NMR spectroscopy, fluorescence methods, and or other analytic techniques. These compounds are capable of binding calcium specifically and with a high dissociation constant; and, therefore, they are highly useful for determining the calcium ion concentrations in organelles or of cells with pathological levels of calcium ion. In addition, they are useful for measuring cytosolic calcium ion levels, having minimal buffering action and perturbative effects.

A. NMR Indicators

One embodiment of the instant invention includes compounds of this invention which are represented by the Formula I:

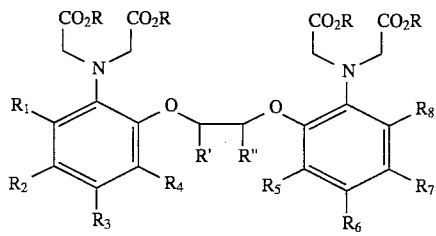

R is selected from the group consisting of hydrogen, acetoxymethyl, and a sodium, potassium or lithium cation. R' and R" are selected independently from the group consisting of hydrogen and lower alkyl; or R' and R", and the carbon atoms to which they are bonded, may be constituents of a 5-membered or 6-membered carbocyclic or heterocyclic ring. $R_1$–$R_8$ are selected independently from the group consisting of hydrogen, lower alkyl, aryl, substituted alkyl, substituted aryl, alkoxy, amino, carboxyl, cyano, halogen, hydroxyl, nitro and chromophoric or fluorescent substituents that are capable of functioning as optical indicators. However, at least one of $R_4$ or $R_5$, is fluorine.

A preferred example of a compound of Formula I is one where $R_4$ and $R_5$ are both fluorine. In another preferred embodiment, R' and R" are selected independently from the group consisting of lower alkyl and hydrogen; and $R_3$–$R_6$ are fluorine.

A particularly preferred example of a compound of Formula I is a compound of Formula II, wherein $R_1$–$R_2$ and $R_7$–$R_8$ are hydrogen, and $R_3$–$R_6$ are fluorine: 1,2-bis(2-amino-5,6-difluorophenoxy) ethane-N,N,N', N'-tetraacetic acid and its derivatives:

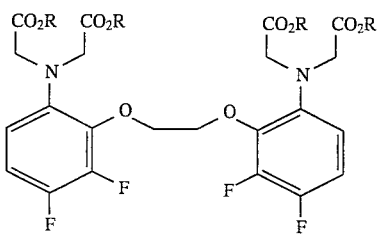

B. Fluorescent Indicators

In another embodiment, the invention includes calcium ion indicators wherein at least one of $R_1$–$R_8$ is selected from the group consisting of chromophoric or fluorescent substituents that are capable of functioning as optical indicators and at least one of $R_4$ or $R_5$ is fluorine.

Preferred examples of these compounds include the following substituent patterns wherein $R_3$ is selected from the group of chromophoric or fluorescent substituents that is capable of functioning as an optical indicator and $R_5$ is fluorine. More preferred examples include those compounds wherein $R_3$ is 6-carboxyindol-2-yl or 2,7-dichloro-6-hydroxy-3H-xanthen-3-one-9-yl.

An especially preferred embodiment is shown in Formula IV where $R_3$ is 6-carboxyindol-2-yl:

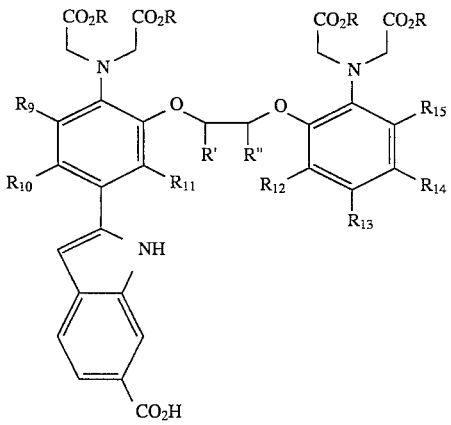

Here, R is selected from the group consisting of hydrogen, acetoxymethyl, and a sodium, potassium or lithium cation. R' and R" are selected independently from the group consisting of hydrogen and lower alkyl; or R' and R", and the carbon atoms to which they are bonded, may be constituents of a 5-membered or 6-membered carbocyclic or heterocyclic ring. $R_9$–$R_{15}$ are selected independently from the group consisting of hydrogen, lower alkyl, aryl, substituted alkyl, substituted aryl, alkoxy, amino, carboxyl, cyano, halogen, hydroxyl, and nitro. However, at least one of $R_{11}$ or $R_{12}$ is fluorine. A preferred example of a compound of Formula I is one where $R_{12}$ is fluorine.

An especially preferred embodiment has the formula:

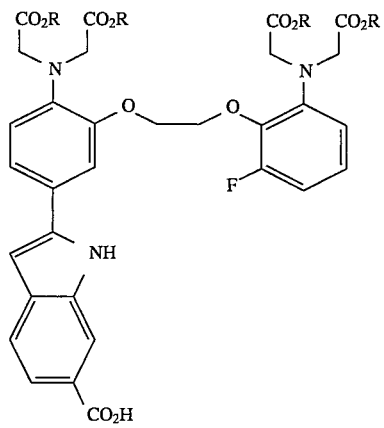

In another embodiment of the invention, $R_3$ is a derivative of 3H-xanthen-3-one-9-yl (Formula IV):

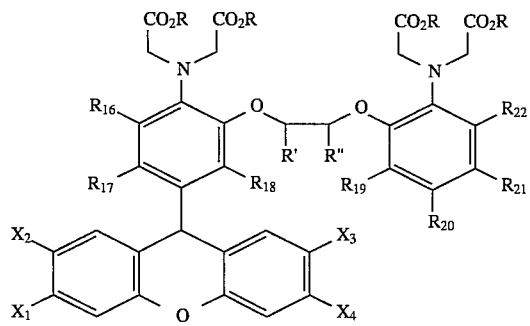

R is selected from the group consisting of hydrogen, acetoxymethyl, and a sodium, potassium or lithium cation. R' and R" are selected independently from the group consisting of hydrogen and lower alkyl; or R' and R", and the carbon atoms to which they are bonded, may be constituents of a 5-membered or 6-membered carbocyclic or heterocyclic ring. $R_{16}$–$R_{22}$ are selected independently from the group consisting of hydrogen, lower alkyl, aryl, substituted alkyl, substituted aryl, alkoxy, amino, carboxyl, cyano, halogen, hydroxyl, and nitro. $X_1$ and $X_4$ are selected from the group consisting of amino, alkoxy, hydroxy, mercapto or alkylsiloxy; in addition, $X_1$ and $X_4$, together with the carbon atoms to which they are attached, may be selected independently from the group consisting of carbonyl, imine or oxime. $X_2$ and $X_3$ are selected from the group consisting of hydrogen, halogen or alkoxy. However, at least one of $R_{18}$ or $R_{19}$ is fluorine.

A preferred example of a compound of Formula IV is one where $R_{19}$ is fluorine. An especially preferred embodiment has the formula:

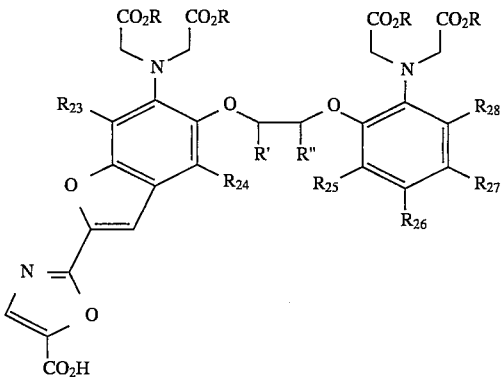

In a further aspect, the invention includes calcium ion indicators comprising a compound of Formula V:

Here, R is selected from the group consisting of hydrogen, acetoxymethyl, and a sodium, potassium or lithium cation. R' and R" are selected independently from the group consisting of hydrogen and lower alkyl, or R' and R", and the carbon atoms to which they are bonded, may be constituents of a 5-membered or 6-membered carbocyclic or heterocyclic ring. $R_{23}$– $R_{28}$ are selected independently from the group consisting of hydrogen, lower alkyl, aryl, substituted alkyl, substituted aryl, alkoxy, amino, carboxyl, cyano, halogen, hydroxyl, and nitro. However, at least one of $R_{23}$ or $R_{28}$ is fluorine.

Preferred examples of calcium ion indicators within this embodiment include the substitution pattern wherein $R_{25}$ is both fluorine.

Especially preferred is the embodiment having the structure:

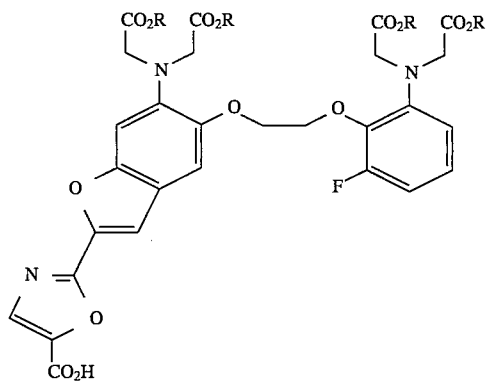

In yet another embodiment, the present invention includes compounds having the formula (Formula VI):

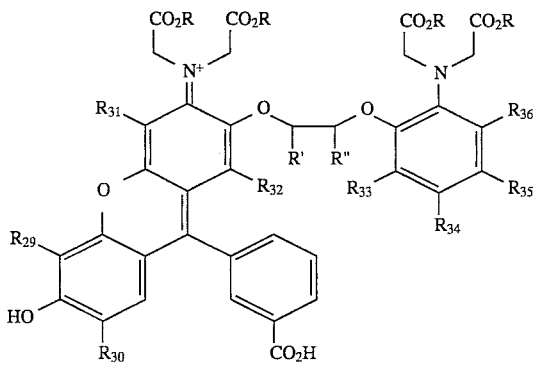

wherein R is selected from the group consisting of hydrogen, acetoxymethyl, and a sodium, potassium or lithium cation; R' and R" are independently selected from the group consisting of hydrogen and lower alkyl; and R' and R", and the carbon atoms to which they are bonded, may be constituents of a 5-membered or 6-membered carbocyclic or heterocyclic ring. $R_{29}$–$R_{36}$ may be selected independently from the group consisting of hydrogen, lower alkyl, aryl, substituted alkyl, substituted aryl, alkoxy, amino, carboxyl, cyano, halogen, hydroxyl, and nitro. However, at least one of $R_{32}$ or $R_{33}$ must be fluorine.

In a preferred compound $R_{33}$ is fluorine. An especially preferred embodiment has the formula:

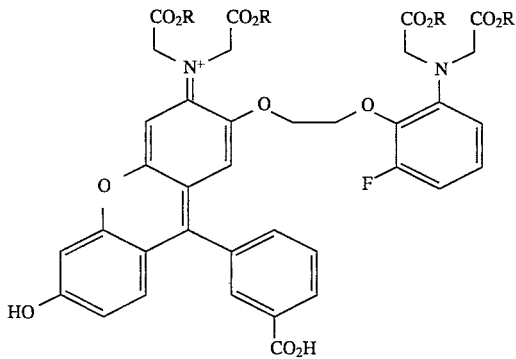

C. Substituents

The compounds of the present invention comprise two aromatic moieties joined by a linkage, —CHR'CHR"—. R' and R" are either hydrogen or lower alkyl, thus producing a linkage such as 1,2-ethanediyl (—$CH_2CH_2$—) or 1,2-propanediyl (—$CH_2CH_2CH_2$—) or 2,3-butanediyl (—$CH_2(CH_2)_2CH_2$—). Alternatively the stereochemical conformation of this simple linkage can be modified by adding bulky substituents, such as t-butyl or i-propyl, or incorporating the linkage into a carbocyclic or heterocyclic ring.

Compounds of Formulas I–VI in which R is acetoxymethyl are useful in the flow cytometric method for measurement of cell parameters such as calcium ion concentration. These compounds penetrate the cell membrane and are cleaved enzymatically within the cell. The resulting charged form of the compound chelates calcium.

The compounds of Formulas I–VI where R is hydrogen or a sodium, potassium or lithium cation may also be used as calcium indicators if they are loaded into the cell through techniques such as intracellular microinjection. These compounds are also useful as intermediates for preparing the corresponding acetoxymethyl esters. III. Synthesis The synthesis of these compounds is achieved readily using materials and techniques which are well-known in the chemical arts ( See, e.g., March, ADVANCED ORGANIC CHEMISTRY (Wiley 1992); Larock, COMPREHENSIVE ORGANIC TRANSFORMATIONS, (VCH 1989); Furniss, et al., VOGEL'S TEXTBOOK OF PRACTICAL ORGANIC CHEMISTRY 5th ed. (Longman 1989); and Green and Wuts, PROTECTIVE GROUPS IN ORGANIC SYNTHESIS (Wiley 1991)). All of the compounds of the invention may be synthesized by analogy to the following examples, using known techniques from commercially available materials or materials whose synthesis is performed using known techniques.

The synthetic pathway for the compound of Formula II (1,2-bis(2-amino-5,6-difluorophenoxy)ethane-N,N,N',N'-tetraacetic acid) is shown below:

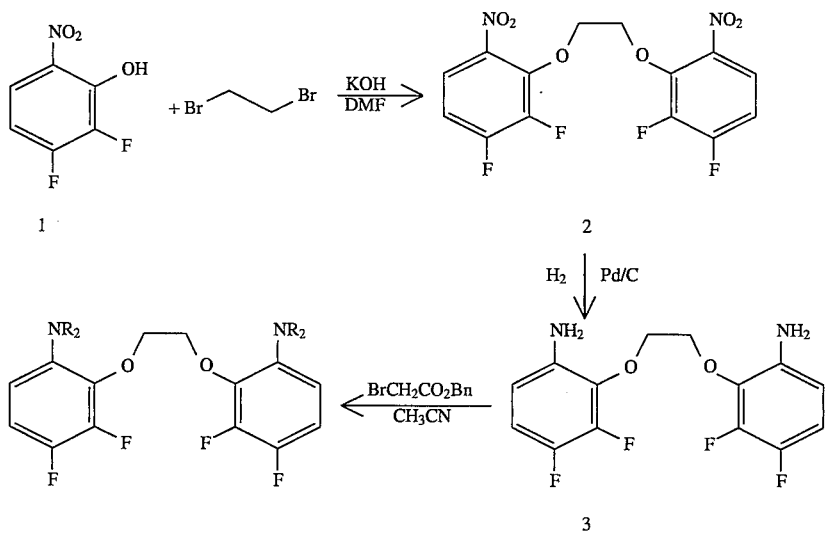

4  R = CH₂CO₂CH₂Ph
5  R = CH₂CO₂H

Starting from commercially available 2-nitro-5,6-difluorophenol (1) (available from Aldrich, Milwaukee, Wis.), 1,2-bis-(2-nitro-5,6-difluorophenoxy)ethane (2) was formed upon the addition of potassium hydroxide and 1,2-dibromoethane (Aldrich) in dimethylformamide solution. This product was hydrogenated over a palladium/carbon catalyst using standard techniques to give 1,2-bis(2-amino-5,6-difluorophenoxy)ethane (3). The desired product, 1,2-bis(2-amino-5,6-difluorophenoxy)ethane-N,N,N', N'-tetraacetic acid tetrabenzyl ester (4) was obtained by reacting a mixture of (3), benzylbromoacetate, and Proton Sponge (1,8bis(dimethylamino)napthalene) in acetonitrile (both available from Aldrich). (Note that for the purposes of illustrating compound 4, R is —CH₂CO₂Ph and —NR₂ denotes the corresponding di-substituted amine —N(CH₂CH₂OPh)₂.) The tetraester (4) was readily saponified to provide the corresponding tetraacid, 1,2-bis(2-amino-5,6-difluoro phenoxy)ethane-N,N,N', N'-tetraacetic acid (5), by reaction of the tetraester in NaOH and methanol followed by acid extraction. (Note that for the purposes of illustrating compound 5, R is —CH₂CH₂OH and —NR₂ denotes the corresponding di-substituted amine —N(CH₂CO₂H)₂.)

The synthesis of Fura-F (Formula V), shown below, is based on published procedures for Fura-2 (Grynkiewicz, et al., *J. Biol. Chem.* 260:3440 (1985)).

2-nitro-4-benzyloxyphenol (6) (See Grynkiewicz) was coupled with 5,6-difluoro-2-nitrophenol using potassium carbonate in dimethylformamide (DMF) solution to form diether (7). The nitro groups were then reduced by hydrogenation over palladium and carbon to give the diamine (8), which was reacted with methyl bromoacetate to give the symmetrically protected diamine (9). (Note that for the purposes of illustrating compound 8, R is H and —NR₂ denotes the corresponding amine NH₂. For compound 9, R represents —CH₂CO₂CH₃ and —NR₂ the corresponding di-substituted amine —N(CH₂CO₂CH₃)₂.) A carbonyl group was then introduced to form compound 10 by reaction of 9 with POCl₃ in DMF. Hydrogenolysis of 10 afforded the corresponding phenol 11, which was reacted with ethylchloromethyloxazole-5-carboxylate to form the cyclic ether 12.

The ester protecting groups were saponified in methanol/potassium to form the desired diamine 13, Formula V. (For the purposes of illustrating compound 12, R' represents —CH₂CH₃ and —NR₂ the corresponding di-substituted amine

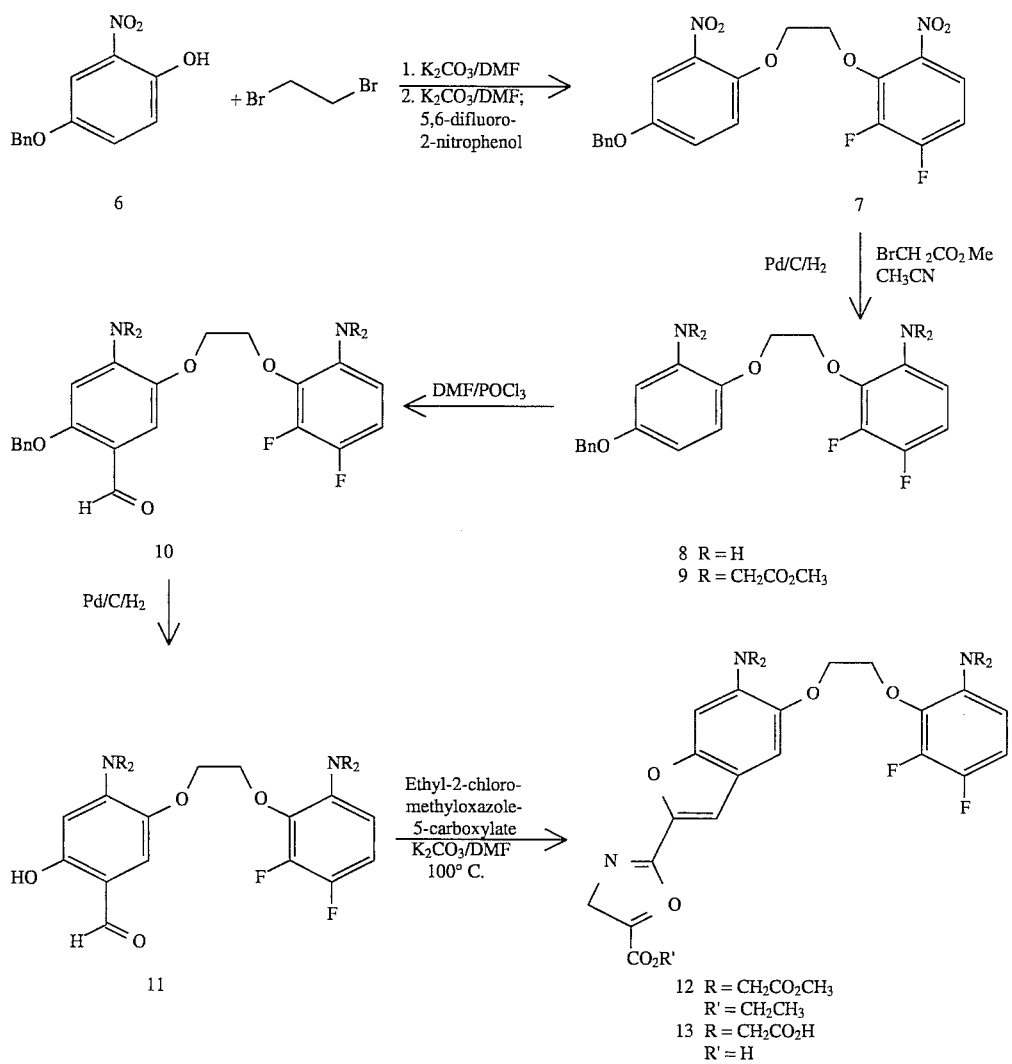
$N(CH_2CO_2CH_3)_2$. Note that for the purposes of illustrating compound 13, R' is H and —$NR_2$ denotes the corresponding amine $N(CH3CO2H)_2)$.
The synthesis of Indo-F (Formula III) is shown in the following schematic, and is analogous to the discussion in Grynkiewicz, et al., cited above.

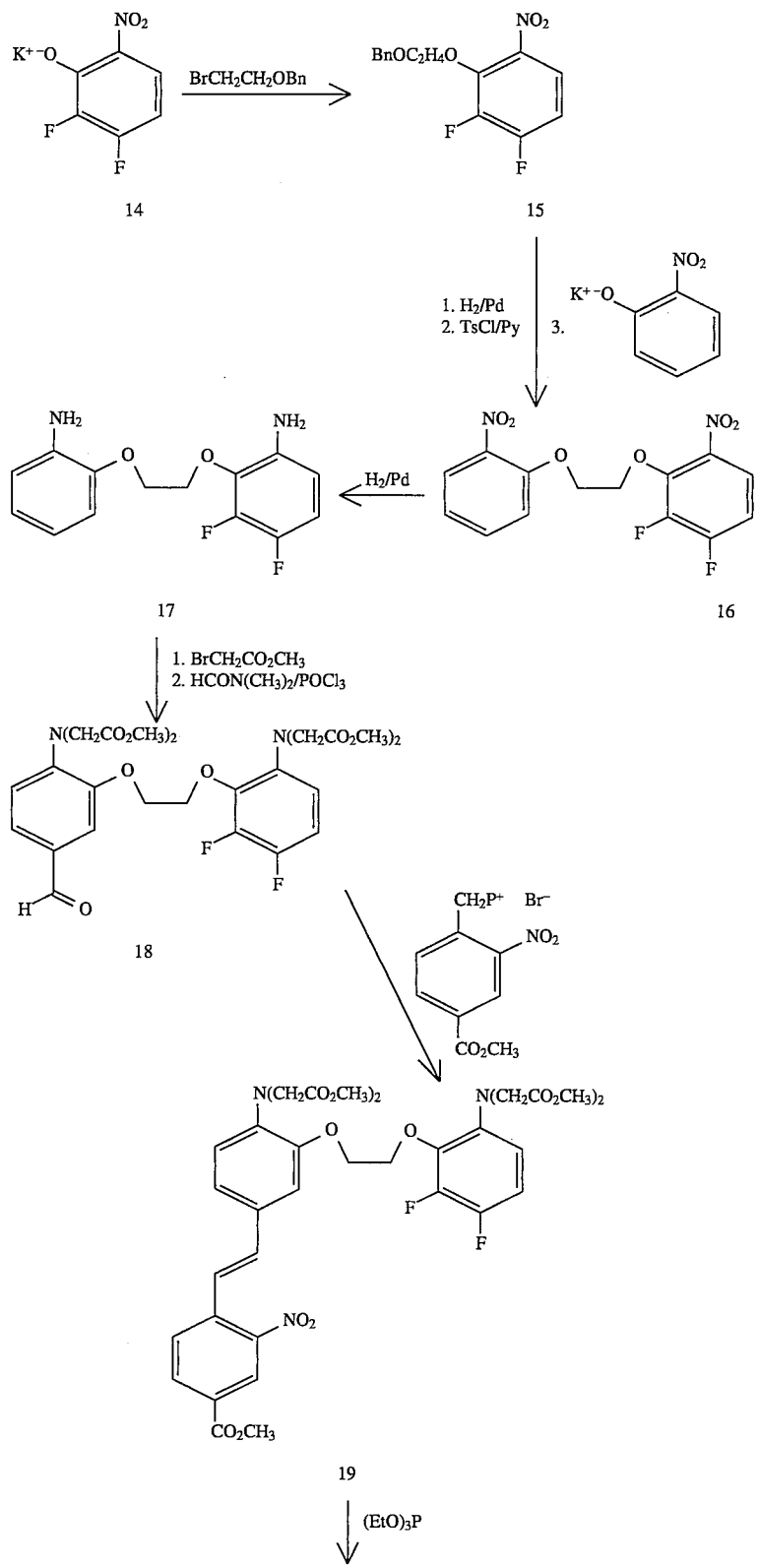

-continued

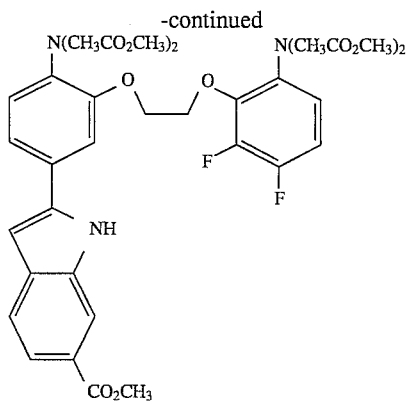

20

↓ KOH

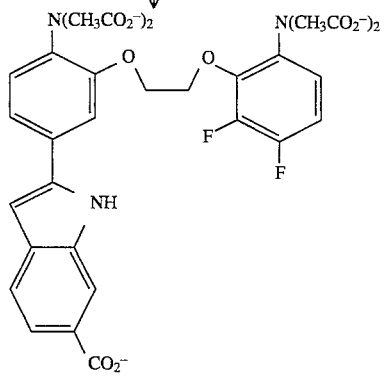

21

Reaction of potassium 2-nitro-5,6-difluorophenoxide (14) with 1-bromo-2-benzyloxyethane provided benzyloxyphenol 15. The benzyl group was next removed by catalytic hydrogenolysis. Reaction with tosyl chloride (TsCl) in pyridine (Py), to tosylate the free hydroxyl group, followed by displacement of the tosyl group with potassium 2-nitrophenoxide afforded the diether 16. Reduction of the nitro groups of 16 to form diamine 17 was accomplished by hydrogenation. The amines were modified by reaction with methyl bromoacetate, and a carbonyl group was introduced by reaction with DMF and $POCl_3$ to generate 18. The olefin 19 was then made by reacting 18 with the Wittig reagent as shown. Cyclization to form 20 was performed using triethylphosphate $((EtO)_3P)$, and saponification with potassium hydroxide (KOH) yielded the desired product 21.

Fluo-F and Rhod-F derivatives (Formula IV) are synthesized as illustrated below by analogy to the descriptions in Minta, et al., *J. Biol. Chem.* 264:8171 (1989).

17

↓ 1. $BrCH_2CO_2tBu$
   2. $Br_2$

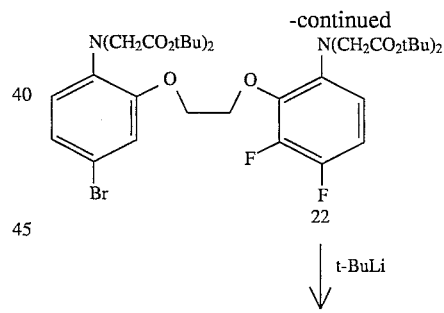

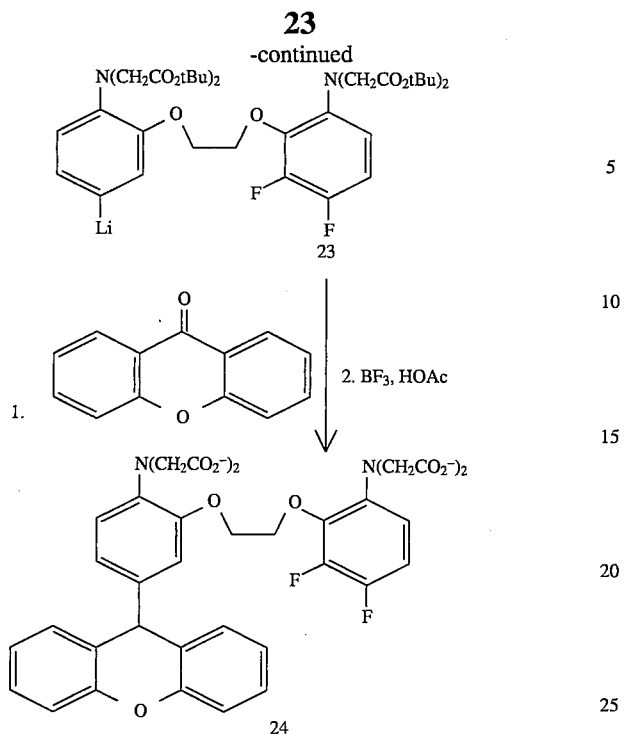

with anthraquinone (available from Aldrich), followed by reaction with a Lewis acid such as boron trifluoride and acetic acid (HOAc) provided an esterified form of the desired product 24, which was converted to the desired product upon saponification by reaction in methanol/KOH.

Fluo-Rhod-F (Formula VI) is synthesized in a manner analogous to IndoF:

Diether 17 was reacted with t-butyl 2-bromoacetate to form the tetra-alkylated amine 22. Lithiation of 22 with t-butyllithium afforded the metallated species 23. Reaction

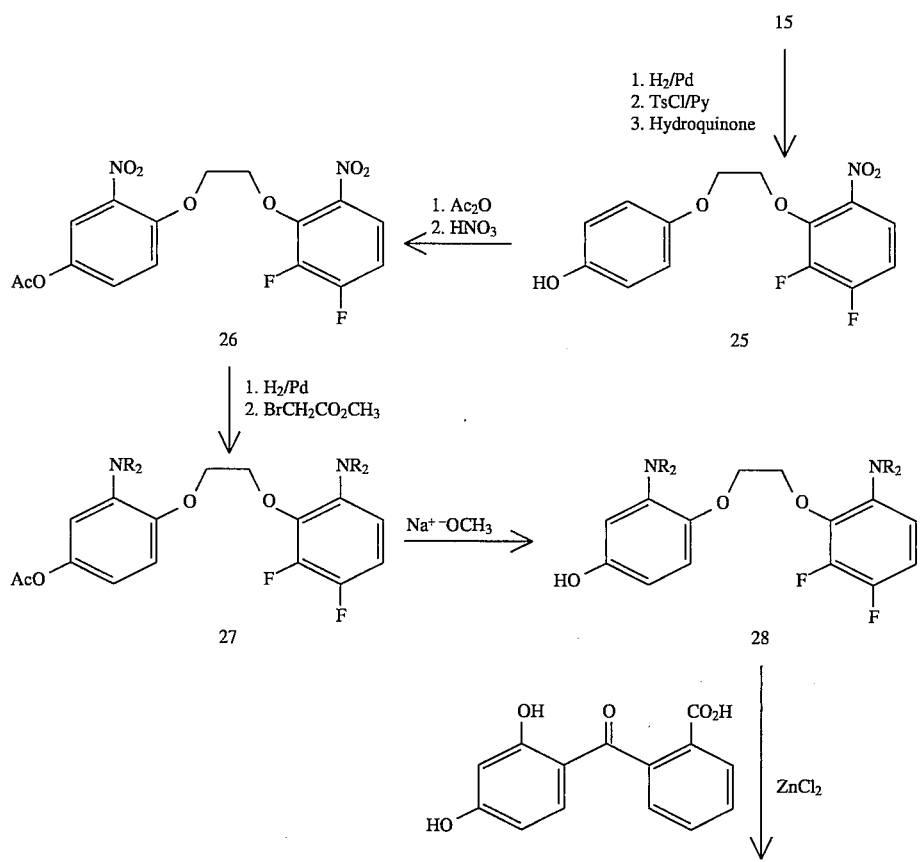

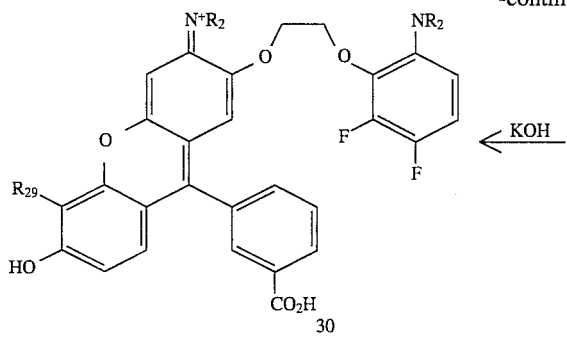
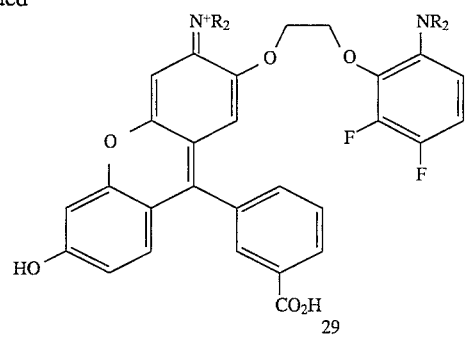

These derivatives are synthesized by analogy to the Fluoro-Rhod series of indicators described by Smith et al. in *J. Chem Soc. Perkin Trans.*, 2:1195 (1993). Compound 15, the preparation of which is described above, was hydrogenolyzed over palladium to remove the benzyl protecting group. This compound was then reacted with tosylchloride in pyridine solution to form the corresponding tosylate. Reaction with the substituted hydroquinone shown yielded the desired product 25. 25 was then reacted with acetic anhydride followed by reaction with nitric acid to yield the bis nitro derivative 26. Reduction of 26 with hydrogen over palladium followed by reaction with methylbromoacetate yielded the tetra-alkylated diamine 27. The acetate group was removed with sodium methoxide to yield product 28. 28 was then reacted with 2'-carboxy-2,4-dihydroxybenzophenone and zinc chloride to produce the polycyclic aromatic derivative 29. Compound 29 was then saponified with potassium hydroxide to yield the desired product 30. (For the purposes of illustrating compounds 27–29, R represents —$CH_2CO_2CH_3$ and $NR_2$ the corresponding di-substituted amine —$N(CH_2CO_2CH_3)_2$. Note that for the purposes of illustrating compound 30, R is H and —$NR_2$ denotes the corresponding acid —$N(CH_2CO_2H)_2$.)

IV. Measurement Techniques

The present invention also includes methods of determining intracellular calcium ion concentrations, wherein a compound of the invention, such as Formula I, is introduced to a cell and the spectrum of the compound is recorded. The features of the recorded spectrum are compared with the spectral features of the compound at known calcium ion concentrations from which the intracellular ion concentration is calculated.

A. Loading

The compounds of the instant invention can be introduced into the sample cells using techniques known in the art. See, e.g., Tsien et al., *J. Cell Biol.*, 94, 925 (1982) and Tsien et al., *Nature*, 295, 68 (1982). In brief, the cells are incubated with the acetoxymethyl ester of the chosen indicator and then washed. Loading efficiency is typically in the range of 10–30% and the fluorescent indicator is used at a final loading level inside the cell of about 10 to 50 μM. For NMR applications, somewhat higher loading levels, in the range of 0.1–0.5 mM are desirable. In some embodiments, the indicator will be microinjected into the cells. See, e.g., Cobbold and Rink, *Biochem. J.*, 248, 313–328 (1987).

B. Measurement Techniques

After the cells have been loaded with a calcium ion indicator of the present invention, the concentration of intracellular calcium ions is determined. The method chosen to detect the presence of calcium ions will, of course, vary with the indicator used and with the nature of the organelle or cell being examined.

Preferred measurement techniques include $^{19}F$ NMR spectroscopy, flow cytometry, and quantitative fluorescence techniques. However, one of skill in the art will appreciate that any other technique capable of detecting at least one physical property which is dependent on whether the intracellular calcium ion indicator is bound to calcium ions or unbound can be utilized with the indicators of the present invention to measure intracellular calcium ion concentration. Any analytical technique capable of detecting these effects can be used in conjunction with the calcium ion indicators of the present invention.

i) $^{19}F$ NMR Spectroscopy

According to the present invention, intracellular calcium ion concentrations can be determined using $^{19}F$ NMR spectroscopy. Measurements have been carried out in several physiological systems of interest, for example in perfused rat heart. The $^{19}F$ NMR shifts of the tetrafluoroBAPTA (Formula II) provide information directly interpretable in terms of the cytosolic $Ca^{+2}$ ion concentration. The $^{19}F$ measurements can be made by using any standard pulsed NMR spectrometer, equipped with a fluorine NMR probe. Typically, at least 100 transients are required for the measurements.

As shown in FIG. 1, two separate $^{19}F$ resonances are observed for the chelator given in Formula II, corresponding to the fluorines at ring positions 6 and 6' (0 ppm), and the fluorines at ring positions 5 and 5'. The latter resonance undergoes a downfield chemical shift and substantial broadening as the calcium concentration is increased. The broadening of the 5,5' resonance is exchange broadening which arises as a consequence of the exchange between uncomplexed and calcium complexed forms. The magnitude of the line broadening will be dependent on the magnetic field strength used. In general, since intracellular resonances of these compounds generally exhibit significant broadening, the additional exchange broadening is not too severe. It is also worth noting that since the calcium exchange is fast on the NMR time scale, loading of the indicator into organelles or other cellular compartments with significantly different calcium ion concentration will result in the appearance of a separate resonances for the 5 and 5' fluorines, so that calcium ion concentrations in each compartment can be determined.

The calcium ion concentration is determined from the observed chemical shift $\delta_o$ the chemical shift of the uncomplexed chelator $\delta_F$, and the chemical shift of the fully complexed chelator $\delta_B$ using the relation:

$$Ca^{+2} = K_D \left[ \frac{\delta_0 - \delta_F}{\delta_B - \delta_0} \right]$$

Use of the above expression assumes fast exchange on the NMR time scale, and neglects changes in the concentration of other interfering ions. Although in general such corrections are small, the expression can be modified to take such effects into account. Generally, the chelators of the invention exhibit pK values of −5.0 and lower, and are relatively insensitive to magnesium ion concentration. Corrections can be readily derived which permit the determination of the $Ca^{+2}$ concentration with knowledge of the pH and magnesium ion concentration. For example, the expression given below includes corrections for protonation and $Mg^{+2}$ complexation.

$$Ca^{+2} = K_D \begin{bmatrix} (\delta_1 - \delta_0) + (\delta_2 + \delta_3 - 2\delta_0)10^{(pK-pH)} + \\ (\delta_4 - \delta_0)10^{(pK+pK'-2pH)} + \\ (\delta_6 + \delta_7 - 2\delta_0)10^{(pMg1-pMg)} + \\ (\delta_8 - \delta_0)10^{(pMg1+pMg2-2pMg)} \end{bmatrix} / [\delta_0 - \delta_5]$$

Figure 2:
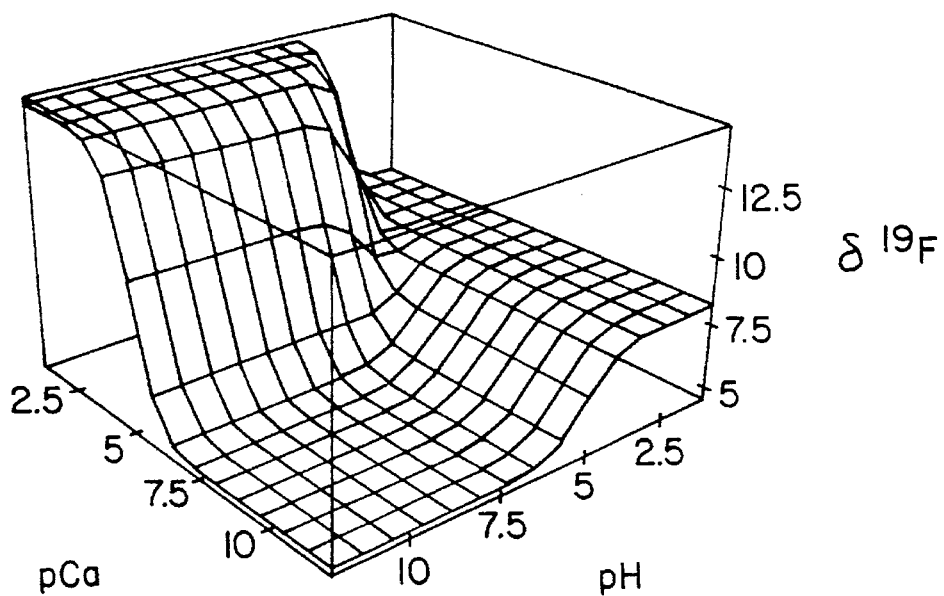
FIG. 2 shows a $^{19}$F shift difference of 5 F relative to 6 F (vertical axis) as a function of pH and pCa, as indicated.
Figure 3:
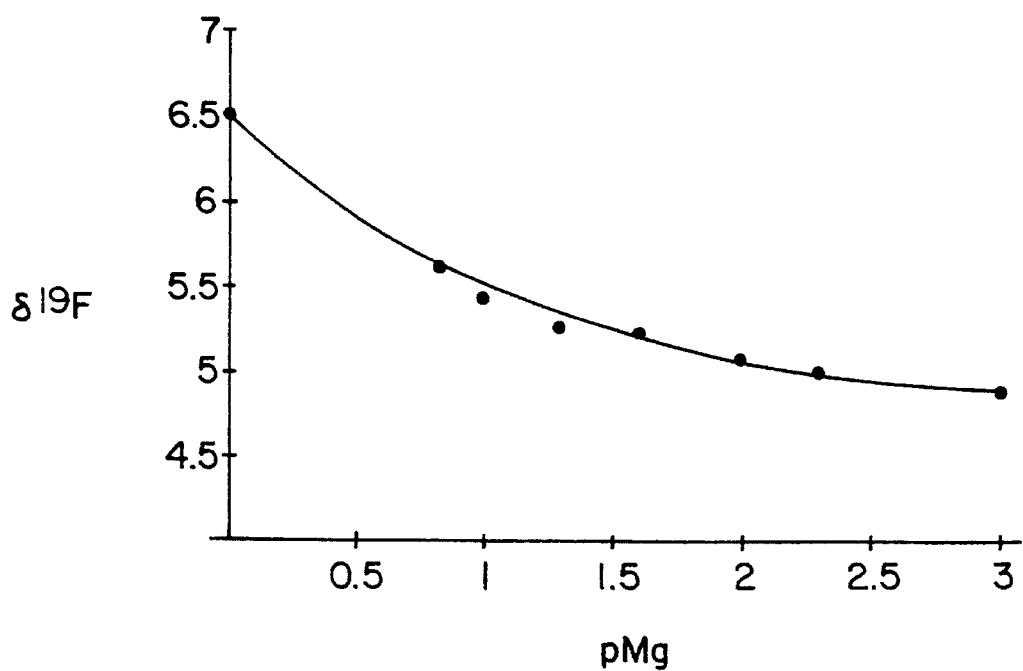
FIG. 3 shows a chemical shift of 5 F resonance of TFBAPTA as a function of added $Mg^{2+}$, expressed as $pMg=-\log_{10}[Mg^{2+}]$.

In the expression above, $\delta_0$ is the observed shift, $\delta_5$ the shift for calcium complexed chelator (analogous to $\delta_B$ above) and the other shifts correspond to various states of protonation and magnesium complexation which are determined by fitting the data in studies in which $Mg^{+2}$ or $H^+$ are varied. The variation of shift with $Ca^{+2}$ and pH is illustrated in FIG. 2. The variation of shift with $Mg^{+2}$ is shown in FIG. 3.

ii) Flow Cytometry

Calcium ions may be detected using an indicator of the present invention and a fluorescence activated cell sorter (FACS) (e.g., FACStar$^{PLUS}$, available from Becton-Dickenson, Franklin Lakes, N.J.) with either a single, or more typically, a dual laser configuration, to monitor the fluorescent indicator. According to this technique, a suspension of fluorescent indicator-loaded cells is transferred to a FACS, where a narrow stream of solution containing the cells passes through two laser beams that excite the fluorescent indicator. Photomultipliers amplify the emissions from the indicator, and a computer determines the magnitude of the fluorescence of each cell as it passes through the laser beam. Cells containing bound indicator have a different fluorescence than those without indicator; allowing the computer to distinguish between them. The computer may also direct the stream to be electrically charged depending on which cells are to be collected. The stream is then broken into droplets by an ultrasonic transducer so that each droplet contains a single cell. If the drop is not charged, it passes straight through a magnetic field and is discarded. If the drop is electrically charged, it will be deflected by a magnetic field and collected in a collection tube. Thus, the use of FACS to detect the indicator substance allows for the simultaneous monitoring of calcium ion concentration and for the collection of those cells with bound calcium ion.

Generally, for use with the fluorescent indicators of the instant invention, the FACS should be equipped with a 560 nm short pass interference filter, and a 405 nm and 485 nm filters for monitoring the indicator. Logarithmic and linear integrated signals generated from the stream-laser intersection can be collected and organized in the form of 256-channel single-parameter histograms. Scatter-gated viable cells (1×10$^4$) are analyzed, and the resulting histograms provide information regarding percentage reactivity, peak channel location, and relative fluorescence intensity.

iii) Quantitative Fluorescence Techniques

According to some embodiments of the present invention, the indicators, when complexed with calcium ions, will emit or excite light at a wavelength different from the wavelength which they emit or excite when not complexed with calcium ions, or have an altered quantum efficiency (i.e., emit at a greater or decreased intensity) when so complexed or exposed. Thus, calcium ion concentration can also be determined using the indicators of the present invention in conjunction with quantitative fluorescence techniques, for example, dual wavelength excitation or emission techniques and the ratio method. (See Tsien et al. *Cell Calcium*, 6, 145–157 (1985)).

Fluorescent embodiments of the present invention can be used to determine levels of ionized calcium. For embodiments such as Formula V for which there is a change in intensity of fluorescence which accompanies calcium ion complexation, the calcium ion concentration may be determined from the fluorescence intensity according to the relation:

$$[Ca^{+2}] = K_D \left( \frac{F - F_{min}}{F_{max} - F} \right)$$

where $K_D$ is the (apparent) calcium ion dissociation constant determined in a model physiological solution, F is the observed fluorescence intensity, $F_{min}$ the minimum intensity obtained a zero $Ca^{+2}$ and $F_{max}$ the maximum intensity obtained at saturating levels of $Ca^{+2}$ ions. (For the case of an indicator which exhibits decreased fluorescence upon $Ca^{+2}$ complexation, the definitions of $F_{min}$ and $F_{max}$ are reversed).

Figure 4:
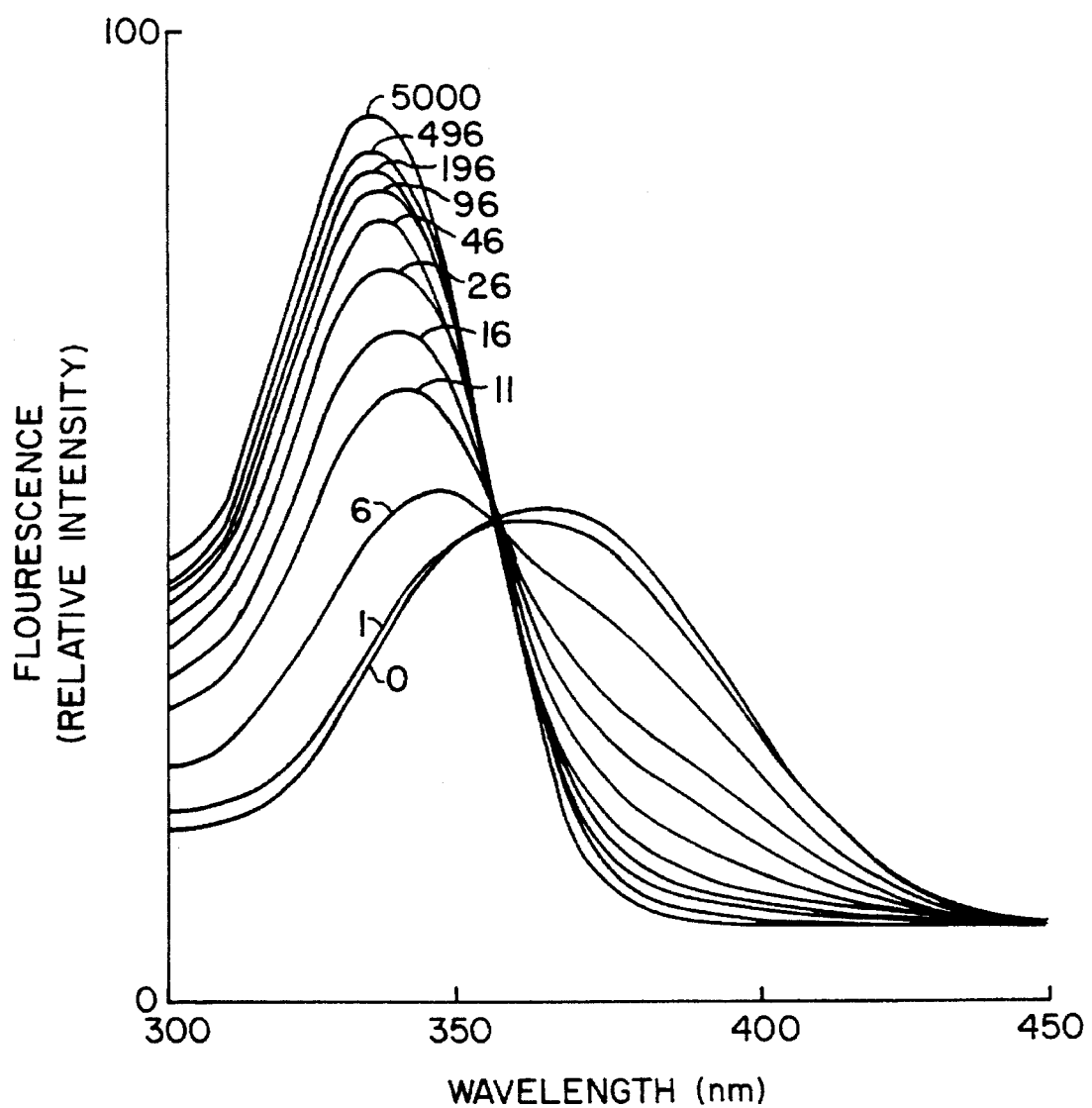
FIG. 4 shows fluorescence excitation spectra of Fura-F (Formula V) as a function of added $Ca^{+2}$ (micromoles). Spectra were scanned at a speed of 100 nm/min, with the emission wavelength set a 510 nm.

Alternatively, for those fluorescent embodiments of the invention such as Formula III and Formula IV, which undergo a fluorescence emission shift (Formula III) or excitation shift (Formula IV), $Ca^{+2}$ concentrations can be determined in a manner analogous to Indo-1 or Fura-2 as described by Grynkiewicz. A fluorescence ratio measurement which compares the excitation or the emission spectrum obtained at two wavelengths, $\lambda_1$ and $\lambda_2$, can be used to determine the $Ca^{+2}$ concentration. This has the advantage that the ratio so obtained is independent of indicator concentration, and so is more useful for imaging applications. In this case, the choice of $\lambda_1$ and $\lambda_2$ is not exactly determined, but in general these are chosen near the maximum in the emission or excitation spectrum for the uncomplexed and for the $Ca^{+2}$-complexed forms of the indicator. The $Ca^{+2}$ concentration can be determined from the relation:

$$[Ca^{+2}] = K_D \left( \frac{R - R_{min}}{R_{max} - R} \cdot \frac{S_{f2}}{S_{b2}} \right)$$

where $S_{f2}$ and $S_{b2}$ are the fluorescence signals of uncomplexed indicator and calcium complexed indicator at a particular wavelength $\lambda_2$, R is the fluorescence ratio obtained at two excitation or emission wavelengths, $\lambda_1$ and $\lambda_2$, $R_{min}$ is the minimum value of this ratio which is obtained at zero calcium, and $R_{max}$ is the maximum ratio obtained at saturating levels of $Ca^{+2}$. Compared to the related, fluorescent Indo-1 and Fura-2 analogs described by Grynkiewicz et al., which have lower $K_D$ values, the fluorine and other substituents on the o-aminophenol ring exert only minor perturbations on the fluorescent properties of the molecule; therefore, compounds of Formula III or IV behave very much as Indo-1 or Fura-2, respectively. This effect is seen in FIG. 4, which shows the excitation spectrum of a compound of Formula V, Fura-F as a function of $Ca^{+2}$ concentration. Calcium levels can be determined on populations of cells suspended in cuvettes, or in individual cells using dual wavelength excitation or emission techniques and the ratio method discussed above (see Tsien et al., *Cell Calcium*, 6, 145–157, (1985)).

In order that the invention described herein can be more fully understood, the following examples are set forth. It should be understood that these examples are for illustrative purposes only, and are not to be construed as limiting this invention in any manner.

EXAMPLES

I. General

Starting materials not described herein are available commercially, are known, or can be prepared by methods known in the art.

In the process described herein for the preparation of compounds of this invention, the requirements for protecting groups are generally well recognized by one skilled in the art of organic chemistry. Accordingly, the use of appropriate protecting groups is necessarily implied by the processes contained herein, although not expressly illustrated.

Isolation and purification of the compounds and intermediates described herein can be effected, if desired, by any suitable separation or purification procedure such as, for example, filtration, extraction, crystallization, column chromatography, thin-layer chromatography or thick-layer chromatography, high-pressure liquid chromatography, or a combination of these procedures. Specific illustrations of suitable separation and isolation procedures are described in the examples hereinbelow. However, other equivalent separation or isolation procedures can, of course, also be used.

II. Synthesis

As discussed above, the synthesis of 5,5', 6,6'-tetrafluoro-BAPTA (Formula II) was carried out as originally described for both BAPTA and 5,5'-difluoro BAPTA starting from commercially available 2-nitro-5,6-difluorophenol. Fura-F was synthesized via the pathway originally described for the preparation of Fura-2. Unless otherwise noted commercially available reagents and dry solvents were used as received. Reactions were carried out under an atmosphere of argon and reaction temperatures refer to the bath. Flash column chromatography was performed with Merck Silica Gel 60 (40–63 μm). Proton sponge is 1,8-bis(dimethylamino)naphthalene.

$^1$H nuclear magnetic resonance ($^1$H NMR) spectra and $^{19}$F nuclear magnetic resonance ($^{19}$F NMR) spectra were measured at 500 MHz and 470 MHz, respectively, on a General Electric GN-500 spectrometer. Unless otherwise noted NMR spectra were obtained in CDCl$_3$ solution. For $^1$H NMR, residual CHCl$_3$ in CDCl$_3$ was employed as the internal standard and assigned as 7.24 ppm downfield (d) from tetramethylsilane (TMS). For $^{19}$F NMR, hexafluorobenzene in CDCl$_3$ was employed as the internal standard.

Compounds Described on Page 23: 1,2-bis-(2-nitro-5,6-difluorophenoxy)ethane (2)

A mixture of 4.59 g (26.2 mmol) of 2-nitro-5,6difluorophenol (1), 3.62 g potassium carbonate and 25 ml of dimethylformamide was heated in an oil bath at 60° C. When the evolution of carbon dioxide had ceased, 1,2-dibromoethane (2.49 g, 13.1 mmol) was added in one portion and heating was continued. The reaction was monitored by thin-layer chromatography (TLC) (9:1 hexane/ethyl acetate) and the rapid appearance of products at retention factor of (R$_f$) 0.6 and R$_f$ 0.4 was noted. After heating overnight, the spot at 0.4 represented almost all of the product. The mixture was cooled and then poured into water. The solid product was filtered off and air dried to yield 2.73 g of crude product. This material was purified by flash chromatography to yield 970 mg of pure crystalline product, melting point (m.p.) 75°–77° . $^1$H NMR: H; 4.65 (s, 4H), 7.01 (m, 2H), 7.67 (m, 2H). $^{19}$F; 13.2 (dd J=18.1 and 5.4 Hz ), 36.7 (m) .

1,2-bis (2-amino-5,6-difluorophenoxy)ethane (3)

A solution of 966 mg of nitro compound 2 in 50 mL of ethyl acetate was hydrogenated at atmospheric pressure using 84 mg of 10% Pd/C as catalyst. Hydrogen uptake was very rapid. The reaction mixture was filtered through Celite and the solvent removed to yield 875 mg of gray crystalline material homogeneous by TLC. A sample was flash chromatographed (3:2 hexane/ethyl acetate) to yield white crystals m.p. 119°–1210°119°–121° C. $^1$H NMR 4.37: (s, 4H), 6.48 (m, 2H), 6.72 (m, 2H); $^{19}$F; 7.10 (dd J=8.8 and 21 Hz), 76 (dd J=21 and 11 Hz).

1,2-bis(2-amino-5,6-difluorophenoxy)etbane-N,N,N',N' tetraaceticacidtetrabenzyl ester (4)

A mixture of 830 mg of 3, 3.90 g benzylbromoacetate, 2.80 g Proton Sponge and 13 mL of acetonitrile was refluxed overnight. TLC (7:3 hexane/ethyl acetate) indicated two closely spaced products at ca R$_f$ 0.65. An additional 1.00 g of benzylbromoacetate was added and heating continued. The lower of the two spots appeared to increase and after 36 hours it was much the larger of the two spots, but an additional spot at greater R$_f$ was now present. The reaction mixture was cooled, ether added and the mixture filtered. The ether solution was washed with pH 2 buffer, water and then dried (MgSO$_4$). Removal of the solvent and flash chromatography of the crude product yielded 984 mg of homogeneous product as a clear light yellow oil. $^1$H NMR: 4.15 (s, 8H), 4.21 (s, 4H), 5.03 (s, 8H), 6.63 (m, 2H), 6.72 (m, 2H), 7.3 (m, 2H). $^{19}$F NMR: 9.02 (dd J=21 and 7.7 Hz), 18.3 (ddd J=21.3, 9.4 and 5.0 Hz ).

1,2-bis(2-amino-5,6-difluorophenoxy)ethane-N,N,N',N'-tetraacetic acid (5)

A mixture of 115 mg of tetrabenzyl ester 4, 2 mL of 0.6M NaOH, and 5 mL of methanol was allowed to stand at room temperature for 48 hours. The organic solvent was removed, 10 mL of water added and the solution extracted with ether. The aqueous solution was acidified with 6N HCl and the precipitated product collected and dried to yield 45 mg of white crystals, m.p. 236°–239° C.

Compounds Described on Page 25: 1-bromo-2-(4-benzyloxy-2-nitrophenoxy)ethane (6)

A mixture of 4-benzyl-2-nitrophenol (1.3 g, 5.3 mmol) and K$_2$CO$_3$ (1.2 g, 8.7 mmol) in DMF (10 mL) was stirred for 10 min. Dibromoethane (1.4 mL, 16.2 mmol) was added to the reaction mixture and heated at 70° C. for 24 hrs. The reaction mixture was diluted with ether (30 mL) and washed with water (20 mL) and brine (20 mL). The ether layer was dried (MgSO$_4$) and concentrated under reduced pressure. The crude product was fractionated by flash chromatography (4:1 hexane/ethyl acetate) yielding bromoethane 6 as a yellow oil (1.3 g, 88%). $^1$H NMR: 3.65 (t, J=5 Hz, 2H), 4.35 (t, J=5 Hz, 2H), 5.05 (s, 2H), 7.0–7.5 (m, 8H).

1-(4-benzyloxy-2-nitrophenoxy)-2(2,3-Difluoro-6-nitrophenoxy) ethane (7).

2,3-Difluoro-6-nitrophenol (0.7 g, 3.7 mmol) was stirred with K$_2$CO$_3$ (0.5 g, 3.7 mmol) in DMF (10 mL) for 10 min. Bromoethane 6 (1.1 g, 3.1 mmol) was added to the reaction mixture and heated at 70° C. for 24 hrs. The reaction mixture was diluted with ether (30 mL) and washed with water (20 mL) and then brine (20 mL). The ether layer was dried (MgSO$_4$) and concentrated under reduced pressure. Fractionation of the crude product by flash chromatography with 4:1 hexane/ethyl acetate provided 7 as a yellow oil (960 mg, 63%). $^1$H NMR: 4.45 (t, J=5 Hz, 2H), 4.71 (t, J=5 Hz, 2H), 5.05 (s, 2H), 7.0–7.7 (m, 10H)

1-(4-benzyloxy-2-aminophenoxy)1-2-(2,3-Difluoro-6-aminophenoxy) ethane (8)

Nitro derivative 7 (800 mg, 1.2 mmol) and Pt/C (100 mg) in EtOAc (20 mL) was stirred for 1 hr under H$_2$. After filtering through Celite with EtOAc, the filtrate was concentrated under reduced pressure to give amino ethane 4 as a white solid (602 mg, 87%). $^1$H NMR: 4.21 (t, J=5 Hz), 4.45 (t, J=5 Hz), 4.97 (s, 2H), 6.3–7.5 (m, 10H). M.P.:

1-(2-Amino-4-benzyloxyphenoxy)-2-(2,3-difluoro-6aminophenoxy)ethane, N,N,N',N'-tetraacetatic acid tetramethyl ester (9)

Proton Sponge®(1.4 g) was added to aminoethane 8 (500 mg, 1.3 mmol) in CH₃CN (15 mL) and the mixture was stirred for 10 min. Methyl bromoacetate (660 mL, 7.0 mmol) was added to the reaction mixture and heated under reflux for 32 hrs. The reaction mixture was diluted with ether (30 mL) and washed with pH 2 solution, water, and then brine. The etheral solution was dried (MgSO₄) and concentrated under reduced pressure. The crude reaction mixture was fractionated by flash chromatography using 1:1 hexane/ethyl acetate yielding tetraacetate 9 as a brown oil (700 mg, 80%). ¹H NMR: 3.61 (s, 6H), 3.66 (s, 6H), 4.11 (s, 4H), 4.15 (s, 4H), 4.19 (t, J=5 Hz, 2H), 4.39 (t, J=5 Hz, 2H), 4.95 (s, 2H), 6.5–7.4 (m, 10H).

1-(2-Amino-4-benzyloxy-5-formylphenoxy)2-(2,3-difluoro-6-aminophenoxy) ethane N,N,N'N'-tetraacetic acid tetramethyl ester (10)

Pyridine (113 mL) was added to tetraacetate 9 (100 mg, 0.1 mmol) in DMF (2 mL) and the mixture was cooled to 0° C. POCl₃ (113 mL, 1.2 mmol) was added dropwise to the mixture and stirred overnight at room temperature. The reaction mixture was quenched with ice and 1M NaOH (10 mL), and then extracted with CH₂Cl₂ (3×10 mL). The CH₂Cl₂ solution was dried (MgSO4) and concentrated under reduced pressure. The crude product was fractionated by flash chromatography with 4:1 hexane/ethyl acetate to give aldehyde 10 (88 mg, 85%). ¹H NMR: 3.65 (s, 6H), 3.75 (s, 6H), 4.15 (s, 4H), 4.1–4.2 (t, J=5 Hz, 2H), 4.25 (s, 4H), 4.30 t, J=5 Hz, 2H), 5.05 (s, 2H), 6.31 (s, 1H), 6.6–6.7 (m, 1H),6.76.8 (m, 1H), 7.25 (s, 1H), 7.2–7.3 (m, 5H), 10.25 (s, 1H).

1-(2-Amino-4-hydroxy-5-formyl-phenoxy)-2-(2,3-difluro-6-aminophenoxy) ethane, N,N,N',N'-tetraacetic acid tetramethyl ester (11)

Tetraacetate 10 (400 mg, 0.6 mmol) with Pd/C (50 mg) in ethyl acetate (20 mL) was stirred for 2 hrs under H₂ and the reaction mixture was filtered through celite to give after removal of solvent pure hydroxy aldehyde 11 (260 mg, 75%) as a pale yellow oil. ¹H NMR: 3.62 (s, 6H), 3.72 (s, 6H), 4.13 (s, 4H), 4.25 (s, 4H), 4.2–4.3 (m, 2H), 4.30 (t, J=5 Hz, 2H), 4.4–4.5 (m, 2H), 6.15 (s, 1H), 6.6–6.7 (m, 1H), 6.7–6.9 (m, 1H), 7.78 (s, 1H), 9.5 5 (s, 1H).

2-[2-(5-carboxyethyloxazole)]-5-[2-(2-bis(carboxymethylmethyl)amino-5,6-difluorophenoxy)]ethoxy-6bis (carboxymethylmethyl)aminobenzofuran (12)

Oven-dried K₂CO₃ (100 mg, 0.7 mmol) was added to the mixture of aldehyde 11 (170 mg, 0.3 mmol) and ethyl-2-chloromethyloxazole[3] (182 mg, 0.9 mmol) in DMF (2 mL) and heated at 100° C. for 1.5 hrs. The reaction mixture was diluted with water (5 mL), acidified with 1M HCl, and then extracted with CHCl₃ (3×10 mL). The CHCl₃ solutions were dried (MgSO₄) and concentrated under reduced pressure. The crude product was fractionated by flash chromatography with 1:1 hexane/ethyl acetate yielding furan 12 as a pale greenish yellow oil (70 mg, 33%). ¹H NMR: 3.62 (s, 6H), 3.72 (s, 6H), 4.12 (s, 4H), 4.25 (s, 4H), 4.2–4.3 (m, 2H), 4.4–4.5 (m, 2H), 6.6–6.7 (m, 1H), 6.7–6.8 (m, 1H), 7.06 (s, 1H), 7.10 (s, 1H), 7.42 (s, 1H), 7.85 (s, 1H). ¹⁹F NMR d: 9.29 (dd J=21 and 7.5 Hz), 18.54 (ddd J=21, 9, and 4.5 Hz).

Hydrolysis of ester 12

KOH (Ca. 10 mg) was added to a solution of furan 12 (ca. 10 mg) in MeOH (1 mL) and water (1 mL) and stirred over night. The reaction mixture was acidified with 1M HCl and filtered through a glass frit with cooled water providing acid 13. Free acid 13 was used as such to determine the $K_D$ value.

The disclosures in this application of all articles and references, including patents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A compound of the formula:

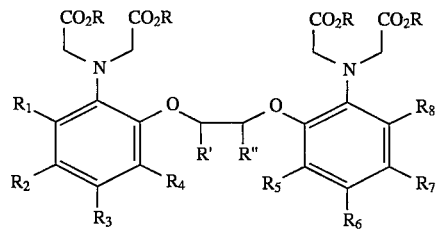

wherein:

R is selected from the group consisting of hydrogen, acetoxymethyl, and a sodium, potassium, ammonium or lithium cation;

R' and R" are selected independently from the group consisting of hydrogen and lower alkyl, or R' and R", and the carbon atoms to which they are bonded, may be constituents of a 5-membered or 6-membered carbocyclic or heterocyclic ring;

$R_1$, $R_2$, $R_7$ and $R_8$ are selected independently from the group consisting of hydrogen, lower alkyl, aryl, substituted alkyl, substituted aryl, alkoxy, amino, carboxyl, cyano, halogen, hydroxyl, nitro, and chromophoric or fluorescent substituents that are capable of functioning as optical indicators; and $R_3$–$R_6$ are fluorine.

2. The compound of claim 1, wherein R' and R" are selected independently from hydrogen and lower alkyl.

3. The compound of claim 2, having the formula:

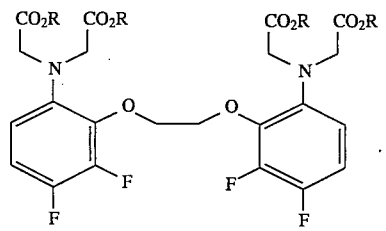

4. A compound having the formula:

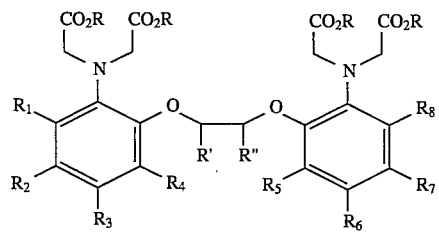

wherein:

R is selected from the group consisting of hydrogen, acetoxymethyl, and a sodium, potassium, ammonium or lithium cation;

R' and R" are selected independently from the group consisting of hydrogen and lower alkyl, or R' and R", and the carbon atoms to which they are bonded, may be constituents of a 5-membered or 6-membered carbocyclic or heterocyclic ring; and $R_1$–$R_8$ are selected independently from the group consisting of hydrogen, lower alkyl, aryl, substituted alkyl, substituted aryl, alkoxy, amino, carboxyl, cyano, halogen hydroxyl, nitro, and chromophoric or fluorescent substituents that are capable of functioninq as optical indicators; provided at least one of $R_1$–$R_8$ is selected independently from the group consisting of chromophoric or fluorescent substituents that are capable of functioning as optical indicators and at least one of $R_4$ and $R_5$ is fluorine.

5. The compound of claim 4, wherein $R_3$ is selected from the group consisting of chromophoric or fluorescent substituents that are capable of functioning as optical indicators and $R_5$ is fluorine.

* * * * *